(12) United States Patent
Kantsevoy et al.

(10) Patent No.: US 8,016,785 B2
(45) Date of Patent: Sep. 13, 2011

(54) GASTROJEJUNAL FEEDING TUBE

(75) Inventors: Sergey V. Kantsevoy, Owings Mills, MD (US); Anthony N. Kalloo, Baltimore, MD (US)

(73) Assignee: Chek-Med Systems, Inc., Camp Hill, PA (US)

(*) Notice: Subject to any disclaimer, the term of this patent is extended or adjusted under 35 U.S.C. 154(b) by 0 days.

(21) Appl. No.: 12/583,355

(22) Filed: Aug. 18, 2009

(65) Prior Publication Data

US 2010/0030138 A1    Feb. 4, 2010

Related U.S. Application Data

(60) Continuation-in-part of application No. 11/799,856, filed on May 3, 2007, now abandoned, which is a division of application No. 11/001,846, filed on Dec. 2, 2004, now Pat. No. 7,220,253.

(51) Int. Cl.
*A61M 29/00* (2006.01)

(52) U.S. Cl. .................................... 604/96.01

(58) Field of Classification Search .................. 606/192, 606/194; 604/96.01, 97.01, 97.02, 101.01, 604/101.02, 101.03, 103.06, 103.07, 104, 604/910
See application file for complete search history.

(56) References Cited

U.S. PATENT DOCUMENTS

| | | | |
|---|---|---|---|
| 4,368,739 A * | 1/1983 | Nelson, Jr. ..................... 604/516 |
| 4,490,143 A | 12/1984 | Quinn et al. |
| 4,496,347 A | 1/1985 | MacLean et al. |
| 4,594,074 A | 6/1986 | Andersen et al. |
| 4,676,778 A | 6/1987 | Nelson, Jr. |
| 4,798,592 A | 1/1989 | Parks |
| 5,057,091 A | 10/1991 | Andersen |
| 5,152,756 A | 10/1992 | Quinn et al. |
| 5,318,530 A | 6/1994 | Nelson, Jr. |
| 6,264,631 B1 * | 7/2001 | Willis et al. ................ 604/96.01 |
| 6,458,106 B1 | 10/2002 | Meier et al. |

OTHER PUBLICATIONS

Literature issued by Boston Scientific Corporation, Natick, MA, USA, for EndoVive™ Standard PEG Kits, (® 2005 Boston Scientific Corporation or its affiliates); copy consists of 7 pages.

* cited by examiner

*Primary Examiner* — Christopher D Koharski
(74) *Attorney, Agent, or Firm* — Eugene Chovanes

(57) ABSTRACT

A feeding tube apparatus is shown, with self propelled features that provide for placement in the postpyloric region of a patient.

11 Claims, 4 Drawing Sheets

GASTROJEJUNAL FEEDING TUBE

CROSS REFERENCE TO RELATED APPLICATIONS

This application is a continuation-in-part of U.S. patent application Ser. No. 11/799,856, now abandoned, filed May 3, 2007, which was a division of U.S. patent application Ser. No. 11/001,846 filed Dec. 2, 2004, now U.S. Pat. No. 7,220,253 dated May 22, 2007.

BACKGROUND OF THE INVENTION (1) Field of the Invention

The invention relates to enteral feeding, and more particularly to gastrojejunal feeding. Specifically, the present invention relates to a feeding tube capable of being placed into the small bowel and anchored with the aid of the natural peristaltic action of the stomach and intestines.

(2) Description of the Prior Art

Feeding tubes, also known as enteral feeding tubes, are widely used in hospitals and nursing homes to provide nourishment to patients that are unable to eat normally. Various gastrojejunal transnasal or transoral feeding systems of the kind relating to this invention are set forth at length in U.S. Pat. No. 6,458,106, incorporated herein by reference.

In the prior art, percutaneous endoscopic gastrojejunostomy (PEG-J) or direct percutaneous endoscopic jejunostomy (DPEJ) are often performed for patients who cannot tolerate gastric feedings or who are at significant risk for aspiration of gastric feeding solution.

Commercially available PEG-J kits use an over-the-wire J-tube method through an existing PEG. These kits allow a 9F to 12F J-tube to be passed through an existing 18F to 28F PEG. After standard PEG placement, the endoscope is reinserted and a guidewire passed through the PEG is grasped in the stomach. The guidewire is advanced with the endoscope into the small intestine. The J-tube is passed over the guidewire into position in the small bowel and plugged into the proximal end of the PEG. Modifications of this technique include maintaining the grasp on the guidewire in the small bowel as the endoscope is withdrawn to help to prevent dislodgment of the J-tube or by using an ultrathin endoscope passed through a 28F PEG tube. The guidewire is fed through the endoscope into position in the small bowel, the endoscope removed, and the J-tube is passed over the wire into the jejunum, where it is the most effective.

Often, however, the feeding tube pulls back into the stomach as the scope is withdrawn and the procedure must be repeated. Notwithstanding such, it is most desirable for the tube to be positioned in the jejunum. Generally, the feeding tube is left in the duodenum with the hope that it will travel on its own into the jejunum. Often, however, the tube migrates back into the stomach instead. Weights have been inserted into the end of the tubes to keep the tube from migrating into the stomach and help with a natural advancement into the jejunum.

These do not work well. The use of a small ball or "bolus" on the end of the feeding tube, as in U.S. Pat. No. 5,057,091, has been tried, but without total success. The art has sought to keep the tube in place in the jejunum after it has been positioned by an endoscope, but often, the tube slips back into the stomach. The fixed bolus is too small to keep the tube in the jejunum.

SUMMARY OF THE PRESENT INVENTION

The present invention uses a balloon capable of being varied in size by inflation and deflation, at the distal end of the feeding tube. First, the balloon is fully inflated after the tube is placed in the duodenum. The fully inflated balloon serves to anchor the feeding tube in the duodenum as the endoscope used to place the tube is withdrawn. The fully inflated balloon prevents the tube from being pulled along with the scope into the stomach.

After removal of the endoscope, the balloon on the end of the feeding tube is then partially deflated to allow duodenal peristalsis to carry the balloon and tube into the jejunum. Such placement is difficult to do endoscopically alone.

Since the balloon can be expanded to a much larger size than a fixed size bolus, it is therefore more effective than the prior art. The balloon, by being deflated below its fully expanded state that is necessary for anchoring purposes, avoids the unwanted effect of causing small bowel obstruction by a fixed size balloon or bolus. Most important, the balloon can be adjusted to a size that the body's natural peristaltic action can have effect but kept small enough that it does not cause obstruction.

The tube has been placed through the abdominal wall.

Figure 1:
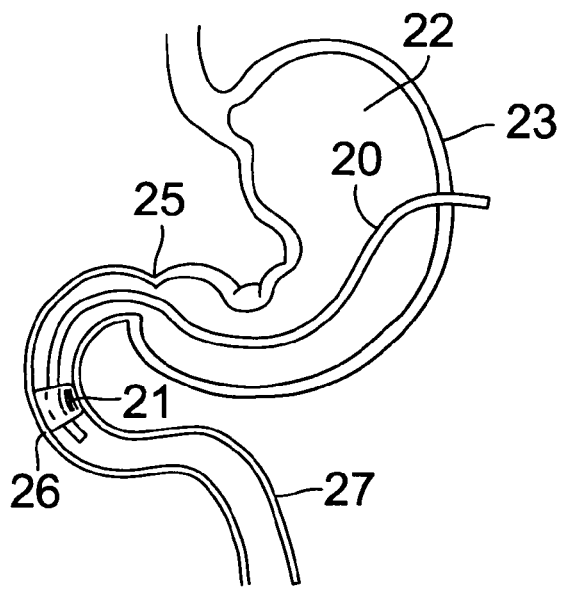
FIG. 1 shows the balloon fully inflated anchoring the feeding tube in the second portion of the duodenum.
Figure 2:
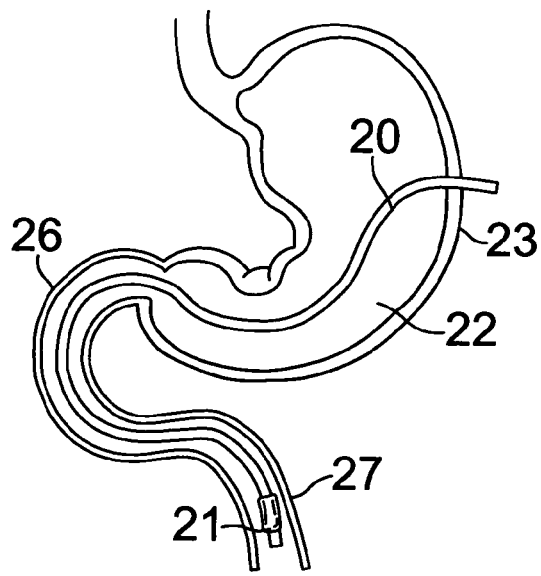

FIG. 2 shows the feeding tube of FIG. 1 with the balloon in the jejunum. It is partially deflated, thus preventing obstruction, but large enough to allow the natural peristaltic action of the small bowel to carry the tube in to the jejunum.

Figure 3:
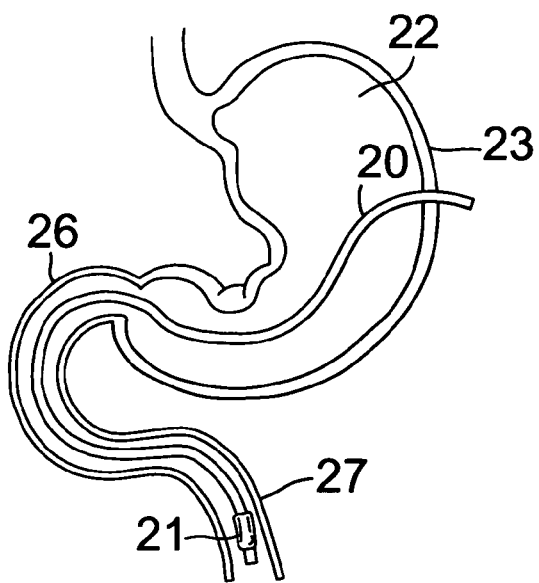

FIG. 3 shows the feeding tube of FIGS. 1 and 2 with the balloon in the jejunum but fully deflated. This is desired after the tube has been carried into the jejunum, thus eliminating any chance of obstruction.

Figure 4:
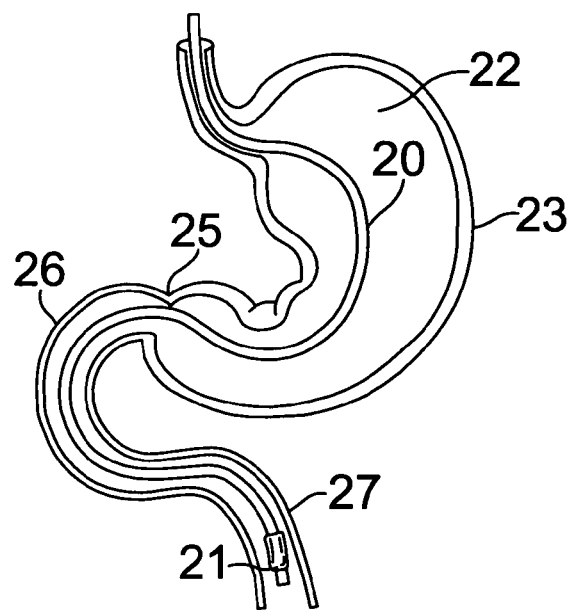

FIG. 4 shows the tube of FIG. 1 through 3 entering the stomach through the esophagus via the nose.

Figure 5:
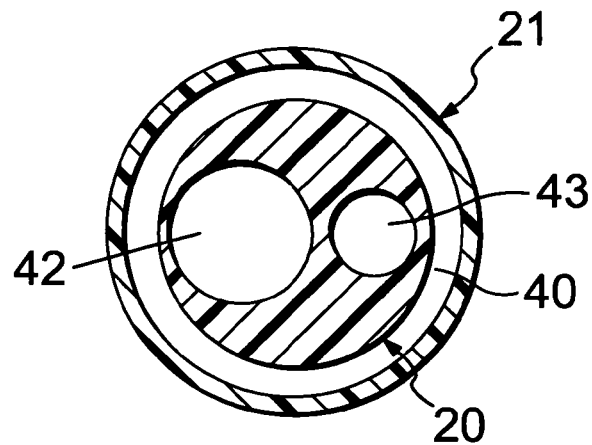

FIG. 5 is a cross section of the feeding tube of FIG. 1 through 3 taken along the tube length above the balloon.

Figure 6:
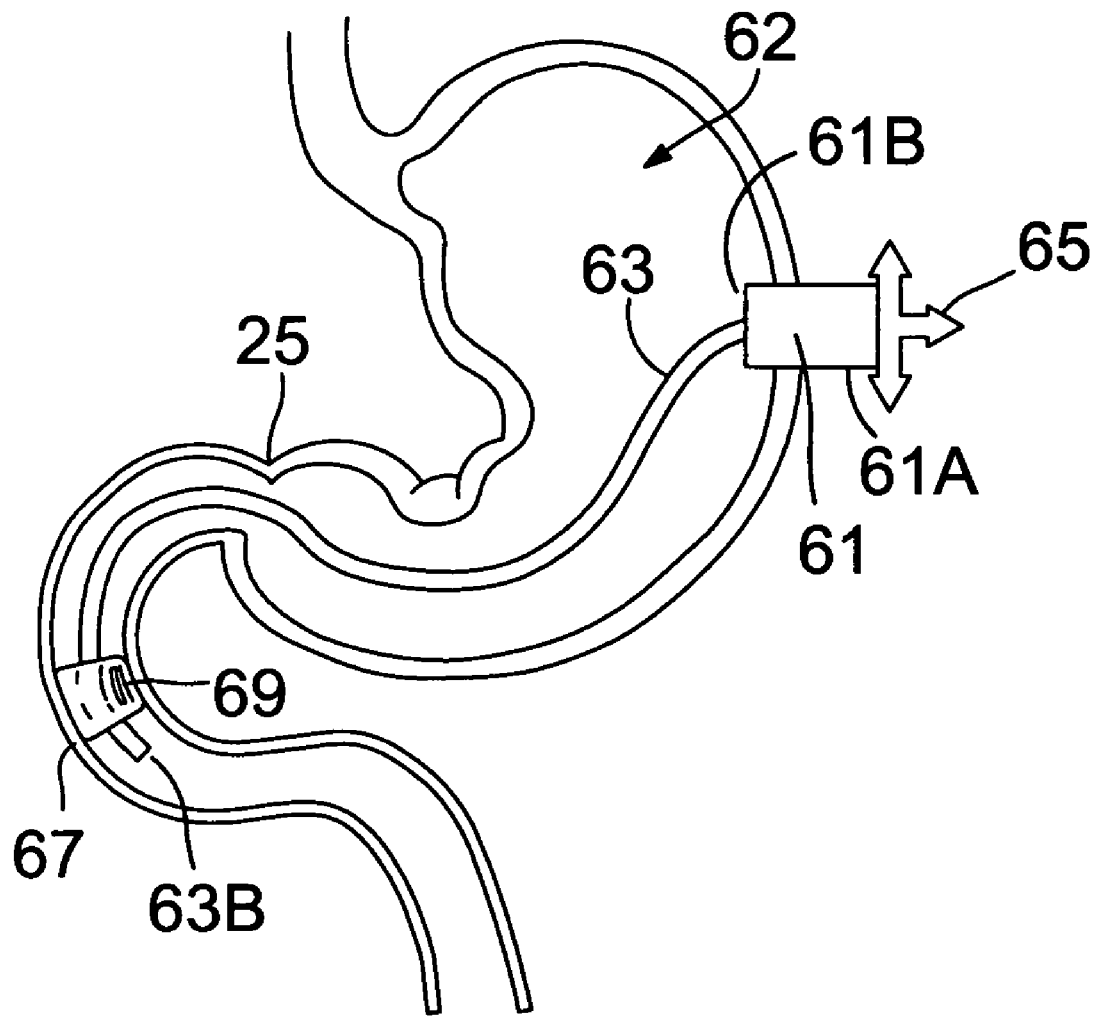

FIG. 6 shows another preferred embodiment.

Figure 7:
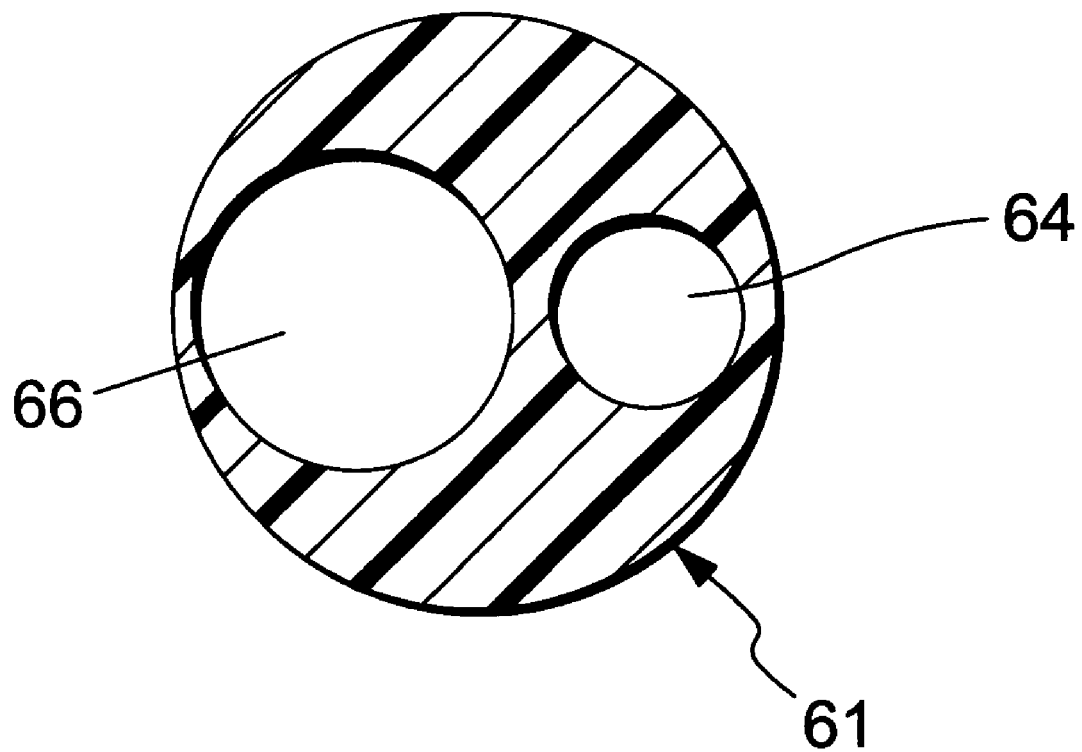

FIG. 7 shows another preferred embodiment.

DESCRIPTION OF PREFERRED EMBODIMENTS

A feeding tube 20, for instance of the type shown in U.S. Pat. No. 4,490,143, incorporated herein by reference, is placed into the position as shown in FIG. 1, using an endoscope in the well-known prior art manner. The feeding tube 20, has at the end thereof an inflatable and deflatable balloon 21 capable of being so inflated and deflated with either air or liquid passed to the balloon through the feeding tube itself during the placement of the tube.

As seen in FIG. 5, the tube 20 has a body 40 containing lumen 42 and lumen 43. Air or other fluids is pumped, or released, through lumen 43 to selectively inflate and deflate balloon 21. Food and liquid is passed along tube 20 through lumen 42.

As seen in FIG. 1 the balloon 21 is partially inflated when the tube 20 is passed into the stomach 22 through the abdominal wall 23 in a well-known prior art manner as shown, for instance, in the '106 patent, with the aid of an endoscope, to a position as shown in FIG. 1.

In this position, the end of the tube has passed through the pylorus 25 into the duodenum 26. The end of tube 20 is held at this location, while the balloon 21 is substantially inflated until it enlarges to contact the wall of the duodenum 26. The endoscope is withdrawn with the tube 20 being held in place by the inflated balloon 21 which extends against the duodenum walls in a fit that retains the tube 21 in position.

As seen in FIG. 2, the balloon 21 is partially deflated as the tube 20 moves through the duodenum 26 into the jejunum 27. The duodenum considers the balloon as a food bolus and begins its peristaltic action to move the balloon 21 along the duodenum into the jejunum. When the tube reaches the desired end point of the placement in the jejunum, as seen in FIG. 3, the balloon 21 is deflated, either partially or fully, so that no possible blockage can occur.

The balloon 21 is left in a deflated condition during a subsequent withdrawal.

FIG. 6 shows another embodiment for enteral feeding through percutaneous endoscopic jejunostomy. In this embodiment a percutaneous endoscopic gastrostomy tube ("PEG tube") 61 has been placed in a patient. The PEG tube has a proximal end 61A and a distal end 61B. The proximal end 61A has an open end for the insertion of fluids, medicines, nutrition and/or apparatus as desired, and the distal end 61B has an open end for termination in a patient's gastric region 62. As shown in FIG. 6, the proximal open end projects outwardly from the patient's abdomen and the distal end terminates in the patient's gastric region. In this embodiment, a single open end is seen. However, PEG tubes with various open ends at the proximal end can be used, as desired. Usually those open ends would share a common channel with termination at the distal end. However, in some embodiments it may be desired to have separate channels associated with a specific open end located at the proximal end terminating in a particular open end of the distal end.

Also shown in FIG. 6 is a percutaneous endoscopic jejunostomy tube ("J-tube") 63 having a proximal end (not shown) and a distal end 63B. The proximal end has an open end for the insertion of fluids, medicines, nutrition and/or apparatus as desired, either with or without a fitting as desired, and the distal end 63B is for terminating in a patient's postpyloric region. Lumens (not shown) extend substantially through the length of J-tube 63, and access is provided to each through fitting 65. As can be seen in the cross sectional view of FIG. 7, lumen 64, which is for fluid access to the balloon, is smaller in diameter than lumen 66 which is for access to the post pyloric region. Moreover, the diameter of lumen 66 may be as much as half or more of the diameter of J-tube 63 for providing desired volume for feeding, medicines, etc.

Returning to FIG. 6, in this and similar embodiments, the J-tube is adapted for retention and is retained within the PEG tube. Once the J-tube is installed within the PEG tube, the proximal end of the PEG tube has projecting therefrom the proximal end of the J-tube, and the distal end of the PEG tube has projecting therefrom the distal end of the J tube. Access to the PEG tube may be provided through fitting 65, so that suction using the J-tube may be performed while the J-tube is retained therein.

At the distal end of the J-tube a balloon 69 is shown. The balloon of this embodiment is for providing self propelling of the J-tube into a desired position within the patient's postpyloric region 67 through intestinal peristaltic action upon the balloon. Before placement of the J-tube within the PEG tube, the balloon is deflated. Post placement, the balloon is inflated for movement through the patient's system via peristaltic activity of the digestive tract. Such movement has been referred to as self propelled movement herein. Access for deflation and inflation is provided through fitting 65. Peristaltic activity causes the J-tube distal end to reach a desired position, often as long as a week or two.

Fitting 65 provides for fixation as well, through a nut (not shown) which provides a lock or anchor between PEG tube 61 and J-tube 63 when fastened, usually at the time of placement. Thus the J-tube anchored within the PEG tube may provide a fixed point for the J-tube's feeding end. Initial placement of a J-tube embodiment through a PEG tube is usually in combination with an endoscope, so as to provide for initial placement of the distal end of the J-tube.

It should be noted that enteral feeding and more particularly gastrojejunal feeding includes nasal, oral and percutaneous feeding. Endoscopic jejunostomy tube embodiments therefore may be used in each of these types of feeding.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

What is claimed is:

1. A feeding tube apparatus for enteral feeding comprising:
an enteral tube, with a proximal end and a distal end, wherein said proximal end has an open end for the insertion of fluids, medicines, nutrition and/or apparatus as desired, and said distal end has an open end for termination in a patient's gastric region;
an endoscopic jejunostomy tube, with a proximal end and distal end, wherein said proximal end has an open end for the insertion of fluids, medicines, nutrition and/or apparatus as desired, and said distal end is for terminating in a patient's postpyloric region;
wherein said endoscopic jejunostomy tube is retained within said enteral tube, with said proximal end of said enteral tube having projecting therefrom said proximal end of said endoscopic jejunostomy tube, and said distal end of said enteral tube having projecting therefrom said distal end of said endoscopic jejunostomy tube;
with said endoscopic jejunostomy tube further comprising self propelling means, wherein said self propelling means comprises a balloon, for placement into a desired position within said postpyloric region; and
wherein said balloon is self propelled through said patient's system via peristaltic activity of said patient's, digestive, tract.

2. A feeding tube-apparatus as in claim 1 where said balloon is adapted to be placed within said enteral tube.

3. A feeding tube apparatus as in claim 1 further comprising an anchor for providing retention of said endoscopic jejunostomy tube relative to said enteral tube.

4. A feeding tube apparatus as in claim 1 where said apparatus is for nasal, oral and percutaneous feeding.

5. A feeding tube apparatus for enteral feeding through endoscopic jejunostomy comprising:
a endoscopic jejunostomy tube, with a proximal end and distal end, wherein said proximal end has an open end for the insertion of fluids, medicines, nutrition and/or apparatus as desired, and said distal end is for terminating in a patient's postpyloric region;
wherein said endoscopic jejunostomy tube is adapted to be placed within an enteral tube;
with said endoscopic jejunostomy tube further comprising self propelling means, wherein said self propelling means comprises a balloon, for placement into a desired position within said postpyloric region; and
wherein said balloon is self propelled through said patient's system via peristaltic activity of said patient's digestive tract.

6. A feeding tube apparatus as in claim 5 where said balloon is adapted to be placed within said enteral tube.

7. A feeding tube apparatus as in claim 5 where said apparatus is for nasal, oral and percutaneous feeding.

8. An endoscopic jejunostomy tube comprising:

a first lumen and second lumen, wherein said first lumen is larger in diameter than said second lumen;

and said first lumen is for post pyloric feeding, and second lumen is for fluid access to a balloon for providing self propelling placement into a desired position within a patient's post pyloric region; and wherein said balloon is self propelled through said patient's system via peristaltic activity of said patient's digestive tract.

9. An endoscopic jejunostomy tube as in claim 8 further comprising said first lumen being at least half the diameter of said tube.

10. An endoscopic jejunostomy tube as in claim 8 further comprising said first and said second lumens extending substantially the length of said tube.

11. An endoscopic jejunostomy tube as in claim 8 where said apparatus is for nasal, oral and percutaneous feeding.

\* \* \* \* \*